United States Patent
Shetty

(10) Patent No.: US 6,685,987 B2
(45) Date of Patent: *Feb. 3, 2004

(54) ENHANCED FATIGUE STRENGTH ORTHOPAEDIC IMPLANT WITH POROUS COATING AND METHOD OF MAKING SAME

(75) Inventor: H. Ravindranath Shetty, Warsaw, IN (US)

(73) Assignee: Zimmer Technology, Inc., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/062,731

(22) Filed: Jan. 30, 2002

(65) Prior Publication Data

US 2002/0127328 A1 Sep. 12, 2002

Related U.S. Application Data

(63) Continuation of application No. 09/267,272, filed on Mar. 12, 1999, now Pat. No. 6,395,327.

(51) Int. Cl.[7] ............................................. A61L 27/00
(52) U.S. Cl. .................. 427/226; 427/2.24; 427/2.27; 427/190; 427/191; 427/199; 427/205; 427/247; 427/398.4
(58) Field of Search ............................ 427/2.26, 2.24, 427/190, 191, 199, 205, 247, 2.27, 398.4; 419/2, 9, 11, 54; 228/121, 222.1, 123.1, 124, 124.5; 148/228, 236, 220

(56) References Cited

U.S. PATENT DOCUMENTS

| 4,013,461 A | | 3/1977 | Elbert |
| 4,082,863 A | | 4/1978 | Dancy et al. |
| 4,714,468 A | * | 12/1987 | Wang et al. ................. 148/408 |
| 4,729,871 A | | 3/1988 | Morimoto |
| 4,834,756 A | * | 5/1989 | Kenna ........................ 128/898 |
| 4,915,361 A | * | 4/1990 | Schwebel et al. ........... 266/249 |
| 5,104,410 A | | 4/1992 | Chowdhary |
| 5,156,321 A | | 10/1992 | Liburdi et al. |
| 5,294,264 A | | 3/1994 | Tiegs et al. |
| 5,308,412 A | | 5/1994 | Shetty et al. |
| 5,443,510 A | | 8/1995 | Shetty et al. |
| 5,462,575 A | * | 10/1995 | Del Corso .................... 419/11 |
| 5,573,604 A | * | 11/1996 | Gerdes ........................ 148/210 |
| 5,734,959 A | * | 3/1998 | Krebs et al. .................. 419/11 |
| 6,132,674 A | | 10/2000 | Compton et al. |
| 6,395,327 B1 | * | 5/2002 | Shetty ........................ 427/190 |

* cited by examiner

Primary Examiner—Shrive P. Beck
Assistant Examiner—Jennifer Kolb Michener
(74) Attorney, Agent, or Firm—Baker & Daniels

(57) ABSTRACT

A method for producing an orthopaedic implant having enhanced fatigue strength. A forged implant substrate having an elongated stem is incorporated with a melting point lowering substance. Then, metal particles are sintered to the substrate, forming a porous layer on the substrate which enhances bone in growth or the mechanical interlock with bone cement. Advantageously, the sintering occurs at a lower temperature than if the substance were not incorporated into the substrate, which in turn results in an enhanced fatigue strength of the inventive implant. The fatigue strength of a forged or cast implant can also be improved by nitrogen diffusion hardening and/or thermally processing the implant after the porous coating is adhered by sintering. Further, the fatigue strength can be further improved by combining incorporating the melting point lowering substance with nitrogen diffusion hardening and/or aging treatment subsequent to sintering.

7 Claims, 1 Drawing Sheet

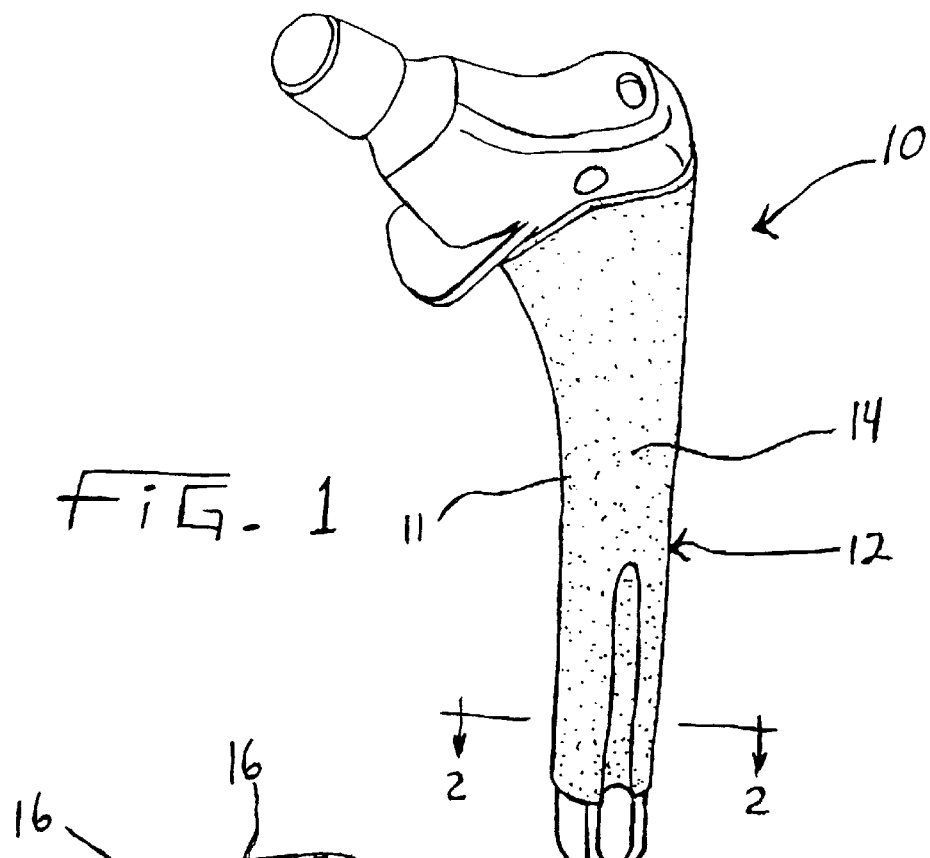
FIG. 1
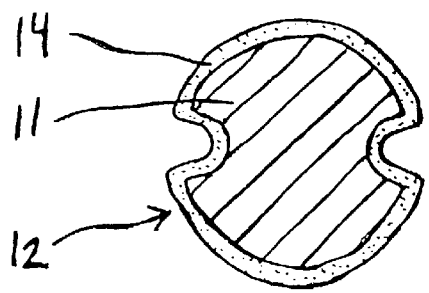
FIG. 3
FIG. 2

ENHANCED FATIGUE STRENGTH ORTHOPAEDIC IMPLANT WITH POROUS COATING AND METHOD OF MAKING SAME

RELATED APPLICATIONS

This is a continuation of application Ser. No. 09/267,272, now U.S. Pat. No. 6,395,327, filed Mar. 12, 1999.

BACKGROUND OF THE INVENTION

This invention generally relates to prosthetic implants having a porous surface attached thereto and more particularly to improving the fatigue strength of a such an implant.

Prosthetic implants for the replacement of a portion of a patient's joints are well-known, and may be constructed of cobalt-chromium-molybdenum or titanium, for example. Similarly, it is known to provide a porous surface layer on the implant to promote fixation by allowing direct bone in growth and interdigitation with the implant. Alternatively, the porous surface may receive bone cement therein to enhance the mechanical interlock with bone cement. The porous surface layer typically takes the form of a plurality of small metallic particles such as beads or a wire mesh. Commonly, the porous surface layer is sintered, diffusion bonded, or welded to the implant. These processes require heating the implant and particles to a temperature sufficient to cause the porous surface layer and implant body to fuse, melt or bond together at their point of mutual contact.

A phenomenon with beaded and/or other textured surfaces is that the texturing creates a "notch effect" on the surface of the implant. If the bonded junctions were viewed in cross section, a small notch would be seen extending into the implant on each side of a contact point between the porous surface layer and the implant. This so-called "notch effect" contributes to crack formation when the implants are cyclically loaded in a fatigue mode.

A related phenomenon with beaded or textured surfaces is that the sintering process by which the beads are typically adhered to the implant creates an annealing effect which reduces the fatigue strength of the implant. This annealing effect is particularly noticeable in forged implants which have a higher fatigue strength, due to working of the metal, than their cast counterparts before bead bonding.

U.S. Pat. No. 5,443,510, assigned to the assignee of the present invention and hereby incorporated by reference, discloses addressing the "notch effect" phenomenon by reducing the number of notches formed. The formation of notches in the implant body can be limited by creating a thin layer of metal mesh on the surface of the implant and then bonding the porous surface layer onto the mesh.

U.S. Pat. No. 5,734,959, assigned to the assignee of the present invention and hereby incorporated by reference, discloses a method for enhancing the bonding between the porous surface layer and the implant. An organic binder such as a water-soluble protein is used to enhance the bonding between the porous surface layer and the implant. During the sintering process, the binder carbonizes and alloys with the metal of the porous surface layer and thereby lowers the melting temperature of the metallic particles at the interface surfaces. Other alloy materials such as silicon can also be suspended in the binder with this method. This patent does not address the notch effect phenomenon.

U.S. Pat. No. 5,308,412, assigned to the assignee of the present invention and hereby incorporated by reference, discloses a method for surface hardening cobalt-chromium based orthopaedic implants by a nitriding or nitrogen diffusion hardening process. The '412 patent is aimed at increasing the wear-resistance properties of the surface of the implant so as to reduce the wear debris produced from articulation against polyethylene, metal, or ceramic counterfaces or by micro-motion of the implant relative to the environment contacting the implant, typically bone or bone cement. The '412 patent suggests that the nitriding process disclosed therein results in minimal or no loss of fatigue properties to the implant.

SUMMARY OF THE INVENTION

The present invention provides an implant having enhanced fatigue strength by incorporating a substance into the implant which reduces the melting point of the substrate prior to sintering the porous layer to the substrate. In so doing, sintering can be performed at a lower temperature, which in turn significantly reduces the fatigue strength loss from a forged implant which occurs during the sintering process.

The present invention also provides a nitriding process and thermal processes to which the implant can be subjected after the sintering process is completed. The nitriding or nitrogen diffusion hardening process and the thermal processes further increase the fatigue strength of a cast or forged implant.

In one form thereof, the present invention provides a method for forming a porous layer on a forged orthopaedic implant. First, an orthopaedic implant substrate formed from a forged metal alloy and having a surface adapted to support a porous layer and a plurality of metallic particles are provided. A substance is incorporated into the forged substrate which substance reduces the melting point of the substrate. The substrate surface and the metallic particles are brought into contact with one another and heated to a temperature less than the reduced melting point, whereby the particles bond to the surface.

In a preferred form, the forged alloy is cobalt-chromium-molybdenum alloy. The melting point lowering substance can be carbon, silicon, nitrogen, niobium, columbium, tantalum, chromium carbides, chromium nitrides, chromium silicides, molybdenum silicides, chromium borides, silicon carbides, silicon nitrides, titanium carbides, titanium aluminides, titanium silicides, zirconium carbides or zirconium silicides.

One advantage of the method described above is that it compensates for the "notch effect" and the reduction in fatigue strength which results from the high temperatures and long times involved in sintering. That is, the method in accordance with the present invention provides a forged implant which maintains most of its fatigue strength through the sintering process.

In another form thereof, the present invention comprises a method for increasing the fatigue strength of an implant having a porous layer thereon. The implant can be formed from either a cast or forged material. An implant substrate formed from a metal alloy and having a surface adapted to support a porous layer and a plurality of metallic particles are provided. The metallic particles are brought into contact with the substrate surface. The metallic particles and implant substrate are heated to a temperature sufficient to sinter the particles to the surface, whereby the particles bond to the surface and form a porous layer. Then, the implant is gas quenched down to at least room temperature. The substrate is then heated to an aging temperature range of about 800° F. to 2100° F. and aged at the aging temperature for 1 to 100 hours.

In a preferred form, the method includes gas quenching the implant to below −90° F. or between −90° F. and −300° F. during the gas quenching step.

One advantage of these thermal processing methods is that they can be used in addition to or separately from the method of incorporating a melting point lowering substance into the substrate.

Another advantage of the inventive thermal processing methods is that they can be used to enhance the strength of forged or cast parts, and can be used with porous coated or uncoated implants.

In yet another form, the present invention provides a method of increasing the fatigue strength of a beaded implant. The implant can be forged or cast. A beaded orthopaedic implant substrate is provided and then exposed to an atmosphere of molecular nitrogen gas or atomic nitrogen at a process temperature within the range of 500° F. to 2400° F. for a process time duration sufficient to achieve increased fatigue strength.

An advantage of the inventive nitriding process in accordance with the present invention is that it significantly improves the fatigue strength of a cast or forged implant. Thus, cast or forged implants subjected to sintering can have their fatigue strength restored by subsequently using the nitrogen diffusion hardening or nitriding process in accordance with the present invention.

Another advantage of the inventive methods of the present invention is that they can improve the mechanical properties of a wide variety of implants, such as for hip, knee, shoulder, elbow and other joints.

BRIEF DESCRIPTION OF THE DRAWINGS

The above-mentioned and other features and objects of this invention, and the manner of attaining them, will become more apparent and the invention itself will be better understood by reference to the following description of embodiments of the invention taken in conjunction with the accompanying drawings, wherein:

FIG. 1 is a perspective view of a hip stem having a porous coat attached thereto in accordance with the illustrated embodiment;

FIG. 2 is a cross sectional view taken along line 2—2 of FIG. 1; and

FIG. 3 is an enlarged fragmentary view illustrating the porous surface of the hip stem of FIG. 1.

Corresponding reference characters indicate corresponding parts throughout the views. Although the drawings represent an embodiment of the present invention, the drawings are not necessarily to scale and certain features may be exaggerated in order to better illustrate and explain the present invention. The exemplification set out herein is not to be construed as limiting the scope of the invention in any manner.

DETAILED DESCRIPTION OF THE INVENTION

As shown in FIG. 1, an orthopaedic implant 10 in the form of hip stem 12 comprises a substrate 11 (FIG. 2) and porous layer 14. Porous layer 14 is comprised of metallic particles. For the purposes of this specification, the term "particles" is to be construed broadly and includes beads, fibers, wire mesh and other known materials and shapes thereof used to form porous layer 14. As shown enlarged in FIG. 3, the particles in the illustrated embodiment are round beads 16. Beads 16 can be bonded to substrate 11 by a known sintering process in which the beads are brought into contact with the substrate and heat is applied, which causes atomic bonding of the beads to the substrate.

It has been found that the fatigue strength of forged (or wrought) cobalt-chromium-molybdenum alloy (ASTM-F1537) implants can be better maintained if the beads can be bonded to the substrate at temperatures below the conventional sintering temperatures, i.e., below 2385° F. The melting point of the substrate can be lowered by incorporating melting point lowering substances, such as metallic or nonmetallic elements into the substrate. Similarly, intermetallic compounds of the same elements can be incorporated into the substrate to lower the melting point thereof. It has been found that a relatively small reduction in melting point of, for example, only about 30–50° F. or more produces a significantly stronger substrate after porous layer 14 is sintered thereto. This is so because much of the reduction in fatigue strength resulting from heating does not occur until the temperature of the substrate approaches its melting temperature. Stated another way, if fatigue strength were plotted as a function of increasing temperature, the resulting graph would be a fairly horizontal line until 50–150° F. below the melting point of the substrate, whereupon a sharp descending curve would appear. Thus, it can be appreciated that relatively small reductions in melting temperature, and in turn sintering temperature, of the surface of the substrate can result in significant preservation of fatigue strength of the implant.

As a related advantage, the time required to successfully sinter the particles to the substrate can be reduced with these melting point lowering substances incorporated into the substrate. The melting point of beads 16 can also be lowered by incorporation of these metallic or nonmetallic elements and compounds into the beads.

Forming of the porous layer on an implant is generally known to one within ordinary skill in the art, and need not be discussed in detail here. Most generally, an orthopaedic implant substrate having a surface adapted to support a porous layer and a plurality of metallic beads are provided. According to the present invention, a melting point lowering substance is then incorporated into the surface of the substrate using the commercially available methods described hereinbelow. The beads are brought into contact with the surface of the substrate and fused thereto by heating to a temperature at which sintering takes place, the temperature being less than the reduced melting point produced by incorporation of the substance. The sintering can be performed in a conventional sintering oven, for example, and as a result, the metallic particles bond to the substrate.

It is to be understood that substrate 11 can be formed from any forged cobalt-chromium-molybdenum or other cobalt base alloys.

Many different elements and intermetallic compounds can lower the melting points of the substrate. These melting point lowering substances include carbon, silicon, nitrogen, niobium, (or columbium), tantalum, chromium carbides, chromium nitrides, chromium silicides, molybdenum silicides, chromium borides, silicon carbides, silicon nitrides, titanium carbides, titanium aluminides, titanium silicides, zirconium carbides and zirconium silicides.

Nitrogen diffusion hardening or nitriding processes involve the surface of the substrate being alloyed with nitrogen by placing the implants and/or beads in a gaseous environment of nitrogen, which results in the alloy having a reduced melting point. Through the process of nitrogen diffusion hardening, nitrides such as $CrN_2$, $CoN_2$ and $MoN_2$ are formed in a surface layer on the substrate. The process of nitrogen diffusion hardening is well-known and is described, for example, in U.S. Pat. No. 5,308,412, assigned to the assignee of the present invention and hereby incorporated by reference. It has been hitherto unknown to use the process of nitrogen diffusion hardening to improve the fatigue strength of a porous coated forged implant.

An ion implantation process can be used to incorporate the melting point lowering substance into the implant substrate. Commercially available ion implantation processes typically involve extracting a stream of ions from an ion source, accelerating and focusing them into a beam which is rastered onto the substrate.

High temperature commercially available coating processes can also be used to coat the implant substrates and beads. Such thermal coating processes include plasma spray coating processes, in which the substance to be incorporated is heated to a molten state and then deposited onto the metal alloy, after which the substance solidifies and mechanically bonds to the substrate.

Blasting the surfaces of the implants with the substances can be accomplished using commercially available blasting processes. The blasting process leaves residues of the melting point lowering substances on the surface of the implants. As a result, the surface of the implants have a lower melting point so that a good metallurgical bond is established between the implant surface and the beads at a lower sintering temperature. Incorporation by blasting process is further advantageous in that the blasting "work hardens" the surface. Additionally, blasting produces a slightly abraded surface which helps the beads to adhere thereto.

Examples of melting point depressants that can be added to the alloy surface using the above-described processes are $CoCO_3$, $Co_2P$, $CoMoO_4$, $CoSi$, $Co_2Si$, $CoSi_2$, $Co_3Si$, $CoS$, $CoS_2$, etc.

Alternatively, sintering of the beads to the implant substrate can be conducted in a nitrogen or carbon atmosphere. For example, the bonding is advantageously performed in a chamber filled with nitrogen gas. Preferably, the atmosphere comprises greater than 99% nitrogen. Likewise, the bonding is advantageously performed in a chamber filled with a carbon containing gas such as carbon dioxide or methane. In addition, the oxygen in the atmosphere is advantageously reduced to limit the effects of oxidation. Processing in such an enriched environment results in carbon or nitrogen being absorbed into the solid alloy substrate, thereupon forming chromium, cobalt and molybdenum carbides and nitrides. The presence of the carbides and nitrides lowers the melting point of the surface of the substrate and consequently lowers the temperature at which sintering of the beads to the substrate takes place.

The process of incorporating melting point lowering substances described above, by itself, minimizes the fatigue strength lost by the forged substrate during the sintering process, as can be seen with reference to Table III, below. However, it has also been found that forged and cast parts can be subjected to nitrogen diffusion hardening or a thermal aging process after the sintering process to add strength to the parts, as described in detail hereinbelow. Furthermore, the subsequent nitriding and aging can be used separately of or subsequently to the above-described incorporation to increase the fatigue strength of the porous coated implant.

Nitrogen diffusion hardening of an implant substrate to improve wear resistance properties is described in U.S. Pat. No. 5,308,412. However, the '412 patent suggests that nitrogen diffusion hardening, at best, will not reduce the fatigue strength of an implant. Surprisingly, the inventors of the present invention have found that nitrogen diffusion hardening performed subsequent to bead bonding of a forged or cast implant actually significantly improves the fatigue strength of the implant. It is anticipated that nitrogen diffusion could be used before bead bonding to lower the diffusion bonding temperature (described above) and/or used subsequent to bead bonding to further improve fatigue strength.

With reference to Tables I and II, below, the improved fatigue strength of porous coated forged Cobalt-Chromium-Molybdenum subjected to nitrogen diffusion hardening can be appreciated. Table I illustrates results derived from a control sample of a forged flat piece of Cobalt-Chromium-Molybdenum bead bonded at a reduced sintering temperature and fatigue tested in a cantilever manner at stress ratio, R=0.1. Even though the test samples were flat, the forging process was performed in accordance with the forging process used for a hip stem, for example. The bead bonding was performed in a sintering oven at 2350° F. for 1 hour. As shown in Table I, the control samples were then cycled 10 million times or until they fractured. Control specimen No. 1 fractured at 55 ksi loading after 3.7 million cycles and specimen No. 2 failed at 60 ksi loading after 2.6 million cycles. Specimen No. 3 did not fail at 57.5 ksi. Thus, this group of samples exhibited a fatigue strength of approximately 55 ksi.

The second set of samples, recorded in Table II, underwent a nitrogen diffusion hardening process after they were bead bonded using the same bead bonding process as used with the controls. The nitrogen diffusion hardening was performed at 2000° F. for 2 hours, using substantially the same procedure described in U.S. Pat. No. 5,308,412. Generally, the nitrogen diffusion hardening comprised exposing the implant substrate to an atmosphere of non-diluted molecular nitrogen gas at a process temperature within the range of 500° F. to 2400° F. for 0.25 to 4 hours. As shown in Table II, no fracture of the nitrogen diffusion hardened substrates occurred until loading of close to 65 ksi. Thus, the nitrogen diffusion hardening process significantly improves the fatigue strength of the forged beaded alloy.

In addition to improving the fatigue strength of a forged alloy, the nitrogen diffusion hardening process can improve the fatigue strength of a cast substrate.

TABLE I

| Spec No. | Run No. | Tested On | Load PSI | HZ | Actual Cycles | Fracture Y = Yes N = No |
|---|---|---|---|---|---|---|
| 1 | 1 | Machine #3 | 49978.12 | 20 | 10000000 | N |
| 1 | 2 | Machine #3 | 55000.00 | 20 | 3670295 | Y |
| 2 | 1 | Machine #3 | 52401.23 | 20 | 10000000 | N |
| 2 | 2 | Machine #3 | 54889.34 | 20 | 10000000 | N |
| 2 | 3 | Machine #3 | 60016.37 | 20 | 2643135 | Y |
| 3 | 1 | Machine #29 | 54991.34 | 20 | 10000000 | N |
| 3 | 2 | Machine #29 | 57572.42 | 20 | 10000000 | N |

TABLE II

| Spec No. | Run No. | Tested On | Load PSI | HZ | Actual Cycles | Fracture Y = Yes N = No |
|---|---|---|---|---|---|---|
| 1 | 1 | Machine #2 | 54998.22 | 30 | 10000000 | N |
| 1 | 2 | Machine #2 | 60011.46 | 30 | 10000000 | N |
| 1 | 3 | Machine #2 | 62444.36 | 20 | 10000000 | N |

TABLE II-continued

| Spec No. | Run No. | Tested On | Load PSI | HZ | Actual Cycles | Fracture Y = Yes N = No |
|---|---|---|---|---|---|---|
| 2 | 1 | Machine #11 | 54995.13 | 30 | 10000000 | N |
| 2 | 2 | Machine #11 | 59968.84 | 30 | 10000000 | N |
| 2 | 3 | Machine #11 | 62526.76 | 30 | 10000000 | N |
| 3 | 1 | Machine #28 | 60049.73 | 30 | 10000000 | N |
| 3 | 2 | Machine #28 | 64871.24 | 30 | 1944553 | Y |

Improvements in fatigue strength can also be obtained by thermal processing after bead bonding using an aging heat treatment.

After the beads are adhered to the implant substrate by sintering, the bead coated implants are cooled from the sintering temperature down to approximately 2100° F. The cooling to 2100° F. can be controlled or allowed to occur naturally in the furnace or oven. Upon reaching 2100° F., the parts are quickly gas quenched down to at least room temperature, or lower. Gas quenching is performed by subjecting the parts to a very cool gas, such as argon or nitrogen, as is widely known in the art. Without wishing to be tied to any specific theory, it is thought that the temperatures obtained during sintering, approximately 2385° F., result in a super saturated condition in the atomic microstructure of the substrate. The fast cooling by gas quenching "locks in" the atomic microstructure formed during sintering temperatures, and allows fine precipitates of chromium and molybdenum carbides to form throughout the substrate upon aging at elevated temperatures.

Thus, after the quenching step, the beaded substrate is heated and aged in temperature range of about 800–2100° F. for 1 to 100 hours, more preferably 1 to 40 hours. Preferably, the heating and aging takes place in an oxygen reduced atmosphere to prevent oxidation. For example, an atmosphere comprising a partial vacuum or an inert gas such as argon are suitable. To a certain extent, the aging time is inversely proportional to aging temperature, so that the time required to reach optimum fatigue strength is reduced with increasing temperature. It is thought that the carbide precipitates formed during the aging process fit within the lattice of the base alloy and increase the hardness and mechanical properties thereof.

The fatigue properties of aged high carbon cobalt-chromium-molybdenum alloy forgings are given in Table III. As shown in Table III, the fatigue strength of conventional high temperature (greater than 2350° F.) sintered cobalt-chromium-molybdenum alloy is reported (Example 1.). The fatigue strength is increased by the above described treatments. Reducing the sintering temperature so that it is less than or equal to 2350° F. (Example 2.) produces a significant improvement as was discussed in conjunction with Table I. It has been found that aging after bead bonding (Example 3.) results in an additive fatigue strength improvement. Finally, performing the sintering at a reduced temperature by incorporating a melting point lowering substance plus nitrogen diffusion hardening (Example 4.), as was discussed in conjunction with Table II, also produces an additive effect. It is believed that any of these processes can be used separately or in combination to improve the fatigue strength of cobalt-chromium-molybdenum alloy implants and that when used in combination they will have an additive effect.

It can be appreciated that the aging process can be useful for applications such as dental implants in addition to orthopaedic implants to improve the fatigue strength thereof. Additionally, the aging process can be used for both cast as well as forged alloys.

TABLE III

Fatigue Properties of Bead Coated High Carbon Co-Cr-Mo Alloy Forgings.

| Process | Fatigue Strength (ksi) R = 0.1; 10,000,000 cycles |
|---|---|
| 1. Conventional High Temperature Sintering Process (Sintering temperature approximately 2385° F.) | 40.0 |
| 2. Reduced Temperature Sintering Process (Sintering temperature = 2350° F.) | 55.0 |
| 3. Reduced Temperature Process Plus Aging (Sintering temperature = 2350° F. and aged at 1400° F. for 2–10 hours) | 60.0 |
| 4. Reduced Temperature Sintering Process plus Nitriding or Nitrogen Diffusion Hardening (Sintering temperature = 2350° F. and nitrogen diffusion hardened in □ 99% $N_2$ at 2000° F. for 0.5–4 hours) | 65.0 |

It has been found that the aging process produces better fatigue strength if the implant substrate is cooled to a cryogenic temperature of between −90° F. and −300° F. (instead of room temperature) during the quenching step. While the exact mechanism by which this cryogenic treatment operates is not understood, it is believed that cooling the substrate to cryogenic temperatures better preserves the super saturated atomic microstructure formed at sintering temperatures.

Specific commercially available alloys that can be used in the aging process, with or without cooling to cryogenic temperatures, include Carpenter Biodur CCM Plus alloy (commercially available from Carpenter Steels of Reading, Pa.), Firth Rixson high carbon alloy (commercially available from Firth Rixson Superalloys Ltd., Derbyshire, England), Teledyne Allvac high carbon alloy (commercially available from Teledyne Allvac or Monroe, N.C.), ASTM F-75, ASTM F-799 and ASTM F-1537.

Hardening and increased fatigue strength of the alloy can also be achieved by slow furnace cooling the sintered Cobalt-Chromium-Molybdenum alloy from sintering or solution treating temperatures. The process parameters are not critical. Cooling in the furnace from the sintering temperature to room temperature over a period of greater than one-half hour produces the desired result. During the slow furnace cooling process, chromium carbides will precipitate in the atomic microstructure lattice and harden the alloy.

While this invention has been described as having an exemplary design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of increasing the fatigue strength of a forged implant, comprising:
   (a) providing a forged orthopaedic implant substrate formed of a cobalt base alloy; and
   (b) exposing the substrate to a nitrogen enriched atmosphere at a process temperature within the range of 500° F. to 2400° F. for a process time duration sufficient to achieve increased fatigue strength.

2. The method of claim 1, wherein the substrate provided in step (a) comprises forged cobalt-chromium-molybdenum alloy.

3. The method of claim 1, further comprising the step of:
   bonding a plurality of metallic particles to the substrate to form a porous layer prior to step (b).

4. The method of claim 1, wherein said process time comprises 0.25 to 4 hours.

5. The method of claim 3, wherein said process time comprises 0.25 to 4 hours.

6. The method of claim 3, wherein said step of bonding a plurality of metallic particles to the substrate to form a porous layer comprises the step of bonding a plurality of metallic particles to the substrate to form a porous layer in a nitrogen enriched atmosphere.

7. The method of claim 1, further comprising sintering a porous layer to the implant substrate prior to step (b).

* * * * *